(12) United States Patent
Dumoulin

(10) Patent No.: US 6,687,530 B2
(45) Date of Patent: Feb. 3, 2004

(54) METHOD AND SYSTEM FOR TRACKING SMALL COILS USING MAGNETIC RESONANCE

(75) Inventor: Charles Lucian Dumoulin, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/683,394

(22) Filed: Dec. 21, 2001

(65) Prior Publication Data

US 2003/0120146 A1 Jun. 26, 2003

(51) Int. Cl.[7] .............................................. A61B 5/055
(52) U.S. Cl. ...................................... 600/423; 324/309
(58) Field of Search ................................ 600/410, 424, 600/423, 422; 324/307, 309

(56) References Cited

U.S. PATENT DOCUMENTS

| | | | |
|---|---|---|---|
| 5,211,165 A | 5/1993 | Dumoulin et al. ........ | 128/653.2 |
| 5,255,680 A | 10/1993 | Darrow et al. ........... | 128/653.2 |
| 5,307,808 A | 5/1994 | Dumoulin et al. ........ | 128/653.2 |
| 5,353,795 A | 10/1994 | Souza et al. ............. | 128/653.2 |
| 5,394,875 A * | 3/1995 | Lewis et al. | |
| 5,437,277 A | 8/1995 | Dumoulin et al. ........ | 128/653.1 |
| 5,947,900 A * | 9/1999 | Derbyshire et al. ......... | 600/410 |
| 6,289,233 B1 | 9/2001 | Dumoulin et al. .......... | 600/410 |
| 6,381,339 B1 * | 4/2002 | Brown et al. ............... | 382/100 |

OTHER PUBLICATIONS

Liu et al. "Comparison of Navigator Echo and Centroid Corrections of Image Displacement Induced by Static Magnetic Field Drift on Echo Planar Functional MRI" (Jan. 16, 2001) Journal of Magnetic Resonance Imaging 13:308–312.*

* cited by examiner

Primary Examiner—Shawna J. Shaw
(74) Attorney, Agent, or Firm—Jean K. Testa; Patrick K. Patnode

(57) ABSTRACT

A method and system for tracking the location of a device within the field of view of a Magnetic Resonance Imaging (MRI) system are provided. The method comprises computing a centroid of signal intensity in a region centered about a location of maximum signal intensity, $L_{max}$ of acquired magnetic resonance (MR) signals corresponding to the device.

11 Claims, 5 Drawing Sheets

METHOD AND SYSTEM FOR TRACKING SMALL COILS USING MAGNETIC RESONANCE

BACKGROUND OF INVENTION

The field of the invention is nuclear magnetic resonance imaging (MRI) methods and systems. More particularly, the invention relates to the tracking of small coils that can be incorporated into interventional devices and other external devices, using MRI methods.

During MR tracking procedures, MR signals are generated throughout the patient using a large transmit coil, but are detected with small receive coils. Locating these coils is accomplished by acquiring the MR signal in the presence of applied magnetic field gradient, Fourier transforming the signal and identifying the position of the most intense frequency-domain signal.

Frequently, tracking coils are almost fully immersed in MR signal generating fluids. This is particularly true for MR tracking catheters. Because the coils detect signals from their entire surroundings, localization of the MR signal can be difficult when the data's pixel size is smaller than that of the coil. Localization becomes even more difficult when the Signal-to-Noise Ratio (SNR) is relatively low. Under these conditions the measured location of the coil appears to hop around the true location of the coil since the local signal maximum varies both spatially and temporally.

One way to improve the precision of the location measurement is to increase the SNR of the acquisition. This can be done by 1) increasing the static magnetic field strength, 2) signal averaging, 3) using larger tracking coils and/or 4) changing the T1 of the MR signal source. Unfortunately, all of these remedies have implications for system cost, resolution (temporal and spatial), and clinical use.

What is needed is a method and system for locating a tracking coil which is insensitive to the location and orientation of the coil or similar tracking device. What is further needed is a method and system for locating a tracking coil with reduced artifacts.

SUMMARY OF INVENTION

In a first aspect, a method for tracking the location of a device within the field of view of a Magnetic Resonance Imaging (MRI) system is provided. The method comprises computing a centroid of signal intensity in a region centered about a location of maximum signal intensity, $L_{max}$ of acquired magnetic resonance (MR) signals corresponding to the device.

In a second aspect, a system for tracking the location of a device within the field of view of a MRI system is provided in which a locator sub-system is adapted to compute a centroid of signal intensity in a region centered about a location of maximum signal intensity.

DETAILED DESCRIPTION

Figure 1:
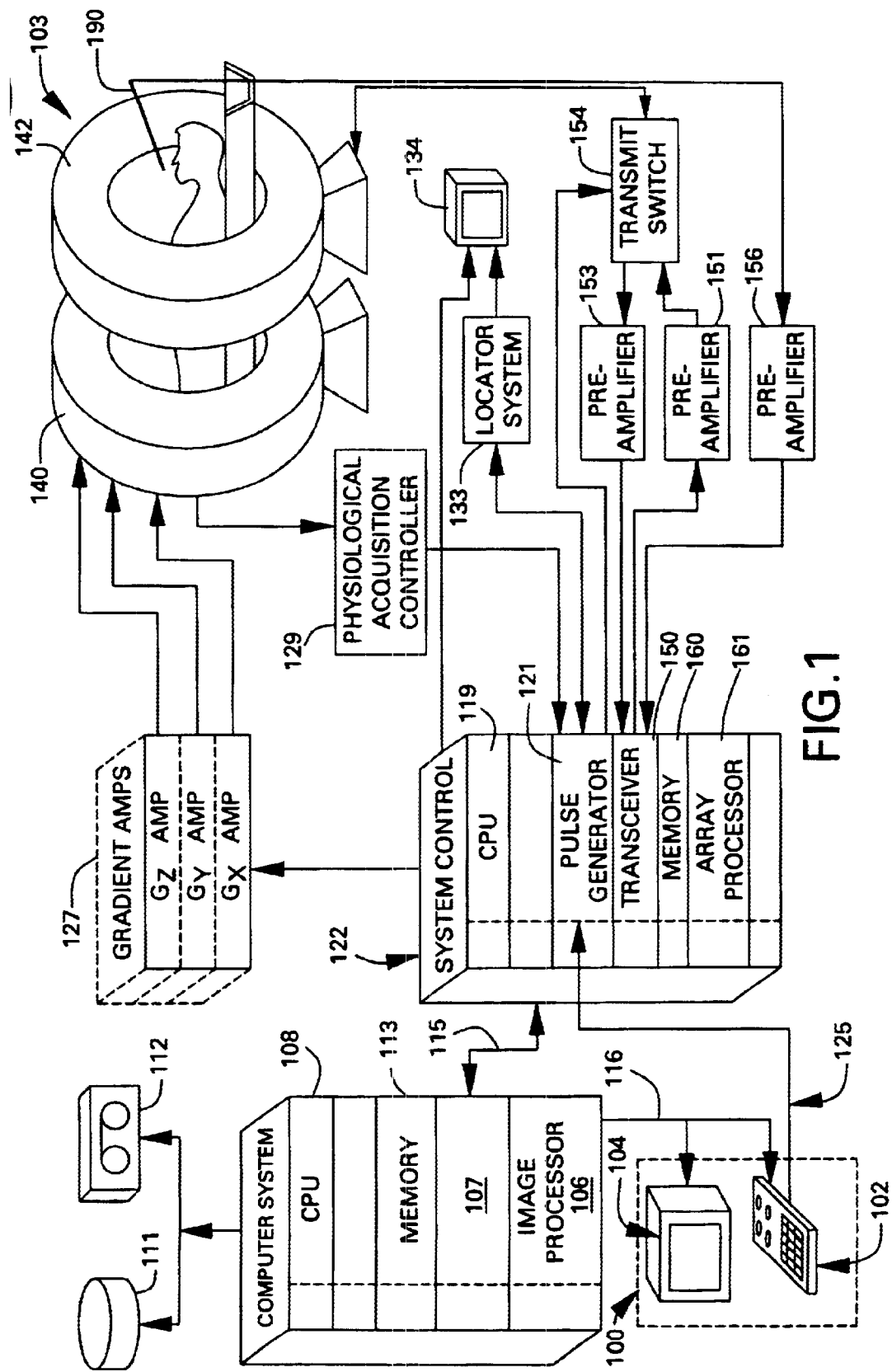
FIG. 1 is a block diagram of an MRI system which employs the present invention.

Referring first to FIG. 1, there are shown the major components of a preferred MRI system that incorporates embodiments of the present invention. The operation of the system is controlled from an operator console 100. Console 100 includes a keyboard and control panel 102 and a display 104. A separate display (not shown) is also located near the magnet system 103 so that system control is also available to a physician attending the subject of a MRI scan. The console 100 communicates through a link 116 with a separate computer system 107 that enables an operator to control the production and display of images on the screen 104. The computer system 107 includes a number of modules that communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 that connects to the operator console 100 through a serial link 125. It is through this link 125 that the system control 122 receives commands from the operator to indicate the scan sequence that is to be performed. The pulse generator module 121 operates the system components to carry out the desired scan sequence. It produces data that indicates the timing, strength and shape of the RF pulses to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a locator sub-system 133. Locator sub-system 133 is adapted to compute the location of a device within the field of view (FOV) of the MRI system in accordance with embodiments of the present invention as described below. As used herein, "adapted to", "configured" and the like refer to mechanical or structural connections between elements to allow the elements to cooperate to provide a described effect; these terms also refer to operation capabilities of electrical elements such as analog or digital computers or application specific devices (such as an application specific integrated circuit (ASIC)) that are programmed to perform a sequence to provide an output in response to given input signals.

The gradient wave forms produced by the pulse generator module 121 are applied to a gradient amplifier system 127 comprised of $G_x$, $G_y$ and $G_z$ amplifiers. Each gradient amplifier excites a corresponding gradient coil in the magnet system 103 to produce the magnetic field gradients used for position encoding acquired signals. A transceiver module 150 in the system control 122 produces pulses which are amplified by an RF amplifier 151 and coupled to an RF coil in the magnet assembly 103 by a transmit/receive switch 154. The resulting signals radiated by the excited nuclei in the patient may be sensed by the same RF coil and coupled through the transmit/receive switch 154 to a preamplifier 153. The amplified MR signals are demodulated, filtered, and digitized in the receiver section of the transceiver 150. The transmit/receive switch 154 is controlled by a signal from the pulse generator module 121 to electrically connect the RF amplifier 151 to the RF coil during the transmit mode and to connect the preamplifier 153 during the receive mode. An RF tracking coil mounted in a medical device 190 is connected directly to a second pre-amplifier 156. As will be explained in more detail below, the medical device 190 is manipulated by the attending physician and MR signals are detected by the tracking coil and processed to locate the position of the medical device. The amplified RF tracking coil signal is input to the transceiver module 150.

The MR signals picked up by a RF coil is digitized by the transceiver module 150 and transferred to a memory module 160 in the system control 122. When an array of k-space image data has been acquired in the memory module 160, an array processor 161 operates to Fourier transform the k-space data into an array of image data which is presented to the attending physician on a display 134. This image data may also be conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

FIG. 1 illustrates an open MRI system, which is designed to allow access by a physician. It is to be appreciated that the embodiments of the present invention described herein are also applicable to a conventional closed MRI system. Referring particularly to FIG. 1, when an intra-operative MR imaging procedure is conducted a patient is placed in the magnet system 103 and a region of interest in the patient is aligned near the system iso-center located between the two, spaced magnet rings 140 and 142. A physician standing between magnet rings 140 and 142 has unrestricted access to the region of interest in the patient.

The images to be produced by the MRI system are prescribed by selecting an appropriate MR imaging pulse sequence to be executed by the pulse generator 121. The location and orientation of the slices or 3D region to be imaged is also prescribed and is determined by the particular patient anatomy the physician wants to see during the procedure being performed. This location and orientation remains fixed until new commands are applied to the pulse generator 121.

The present invention employs a tracking coil which is mounted in a medical device used by the physician. As will be described in more detail below, tracking coil measurement acquisitions are interleaved with the acquisition of image data and MR tracking signals are detected by a tracking coil, amplified by preamplifier 156 and coupled to transceiver module 150. These signals are then Fourier transformed by the array processor 161. The transformed MR tracking data is used by the locator sub-system 133 to produce an icon representing the medical device for display 134. The icon is overlaid on the MR image of the patient anatomy at the location indicated by the tracking coil.

Figure 2:
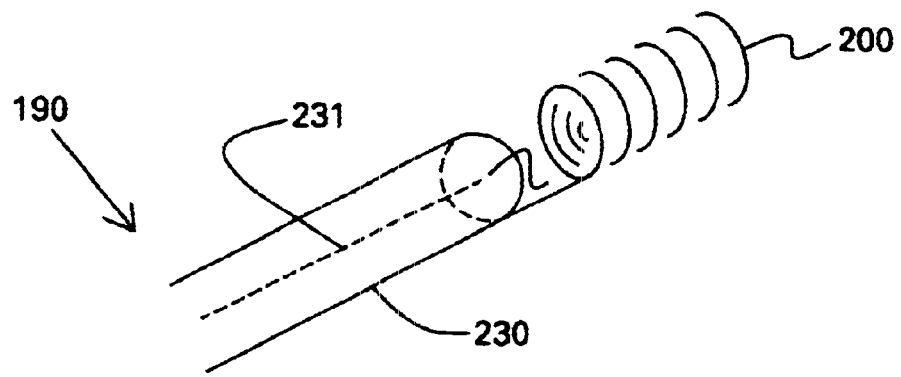
FIG. 2 is a schematic diagram of a tracking coil to which embodiments of the present invention are applicable.

Referring particularly to FIG. 2, a medical device 190 designed for insertion into a patient includes a small RF tracking coil 200 mounted in its operative end. The medical device 190 may be, for example, a guide wire, a catheter, an endoscope, a laparescope, a biopsy needle, an ablation device or other similar devices. Embodiments of the invention described herein are also applicable for non-invasive devices such as external coils used in tracking. Since the tracking coil 200 is small, its region of sensitivity is small and it only picks up MR signals from excited spins in its immediate vicinity. These MR signals are coupled to the T/R switch 154 in the MRI system by a pair of coaxial conductors (230, 281). These conductors are typically encased along with the tracking coil 200 in an outer shell (not shown) of the medical device 190.

Figure 3:
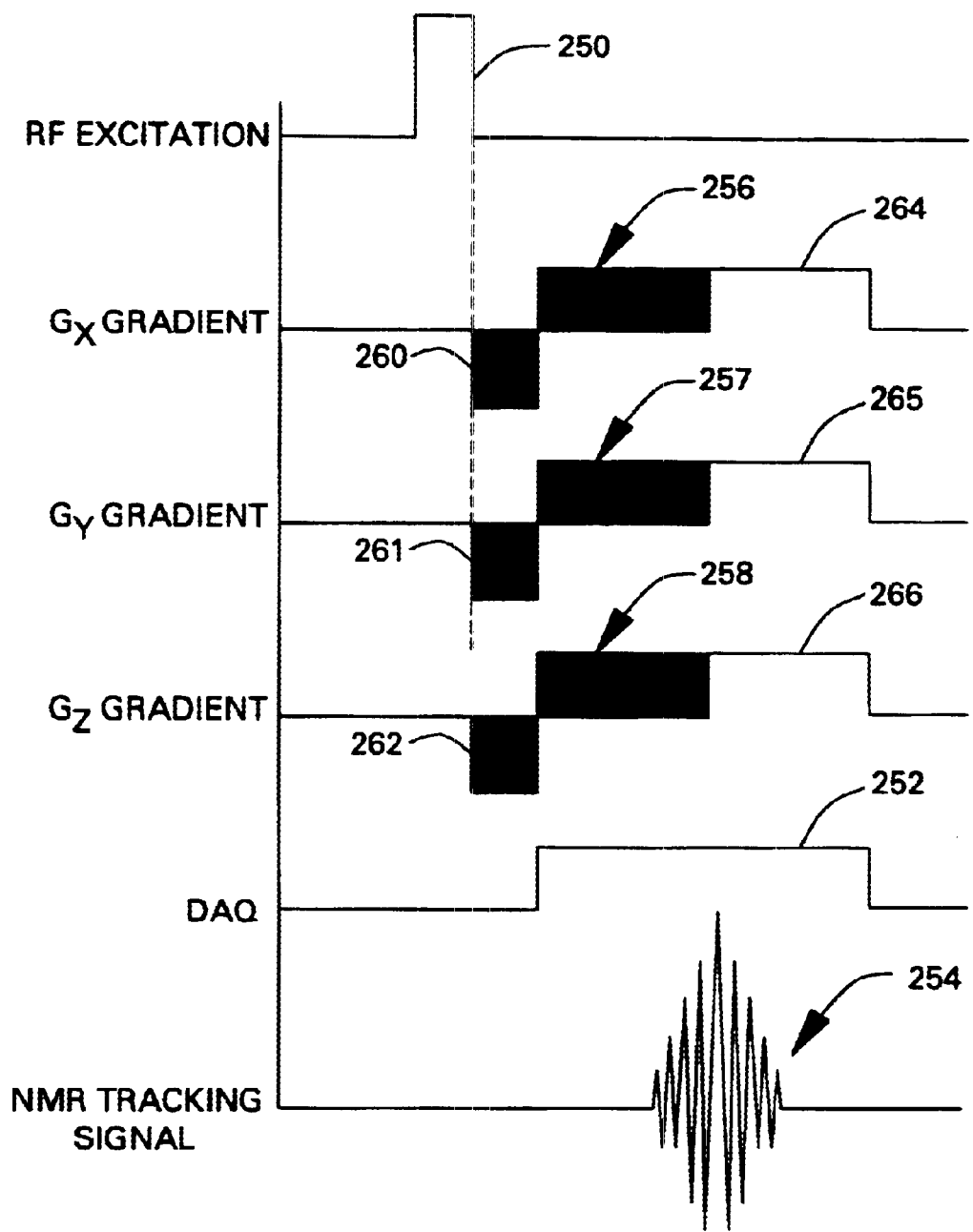
FIG. 3 is a graphic representation of an MR pulse sequence used by the MRI system of FIG. 1 to measure the position of the tracking coil of FIG. 2.

The position of the tracking coil 200 relative to the gradient iso-center is measured using a position measurement MR pulse sequence shown in FIG. 3. This gradient recalled echo pulse sequence yields a signal that is essentially a Fourier transform of a projection of the coil location along the readout gradient direction. Assuming that the tracking coil 200 is small, its position $S_1$ is modeled by:

$$S_1 = \frac{\Delta \omega}{\gamma G_1} \quad (1)$$

where $\Delta \omega$ is the measurement angular frequency of the gradient echo signal relative to $\omega_0$, the Larmor frequency $\gamma$, is the gyromagnetic ratio of the nuclear spins, and $G_1$ is the applied readout gradient. The three-dimensional position of each tracking coil 200 can be identified from three linearly independent gradient echoes.

Figure 4:
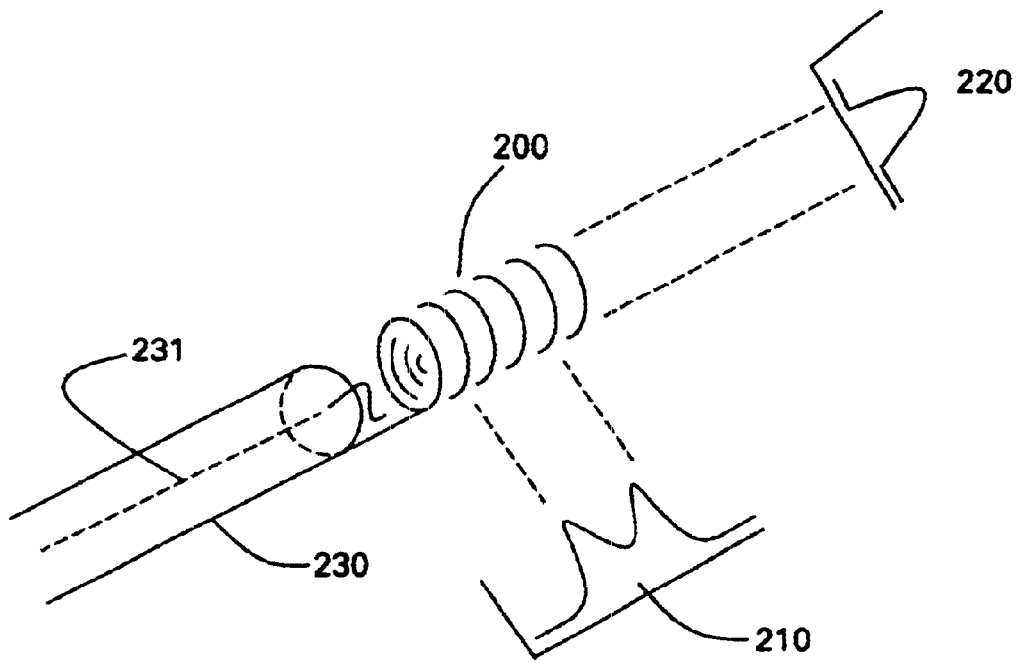
FIG. 4 is a schematic diagram of a tracking coil and associated sensitivity profiles to which embodiments of the present invention are applicable.

The geometry of a typical tracking coil is shown in FIG. 2. This coil has a solenoid geometry and a relatively well characterized sensitivity profile. When a tracking coil is used, however, the distribution of signal detected by the coil is highly dependent upon the orientation of the coil with respect to each of the applied magnetic field gradients. The radial and axial sensitivity profiles of a typical tracking coil are shown in FIG. 4 at 210 and 220. Note that when the spatial-encoding gradient is applied along the length of the tracking coil, a complicated sensitivity profile 210 is obtained and that conventional tracking algorithms will select the location of maximum pixel intensity as the location of the coil.

Referring particularly to FIG. 3, the tracking coil measurement pulse sequence includes a non-selective RF excitation pulse 250 that is applied to the MRI system whole body RF coil. It has a selected flip angle, typically chosen to be between 10 and 60 degrees and it produces transverse magnetization in spins located throughout the magnet bore. Three gradient wave forms 256, 257 and 258 are then applied to produce a gradient recalled MR echo signal. The T/R switch 154 is controlled during a data acquisition window 252 to receive an MR tracking signal 254 from the tracking coil 200. The three gradient wave forms 256, 257 and 258 are applied along the respective $G_x$, $G_y$ and $G_z$ gradient axes, and each includes a respective de-phase lobs 260, 261 and 262 and a respective readout lobe 264, 265 and 266. As indicated by the cross-hatching, the area of each de-phasing lobe 260–262 is equal to one-half the area of the respective readout lobes 264–266.

In the measurement pulse sequence of FIG. 3, all of the gradients waveforms 258–258 all have the same polarity, which is designated herein as "+". "−" indicates the polarity of gradient pulses 260–262 having a polarity opposite that of waveforms 258–258. This pulse sequence is performed a total of four times with the polarity of the $G_x$, $G_y$ and $G_z$ gradient pulses selectively reversed as set forth in Table 1.

TABLE 1

|  | $G_x$ | $G_y$ | $G_z$ |
|---|---|---|---|
| acquisition 1 | − | − | − |
| acquisition 2 | + | + | − |
| acquisition 3 | + | − | + |
| acquisition 4 | − | + | + |

As indicated above, the four MR tracking signals 254 are Fourier transformed to produce four corresponding projections $P_1$, $P_2$, $P_3$ and $P_4$. Together, these four projections form an MR tracking data set from which the x, y and z coordinates of the tracking coil position can be calculated with linear equations known to those skilled in the art.

Figure 5:
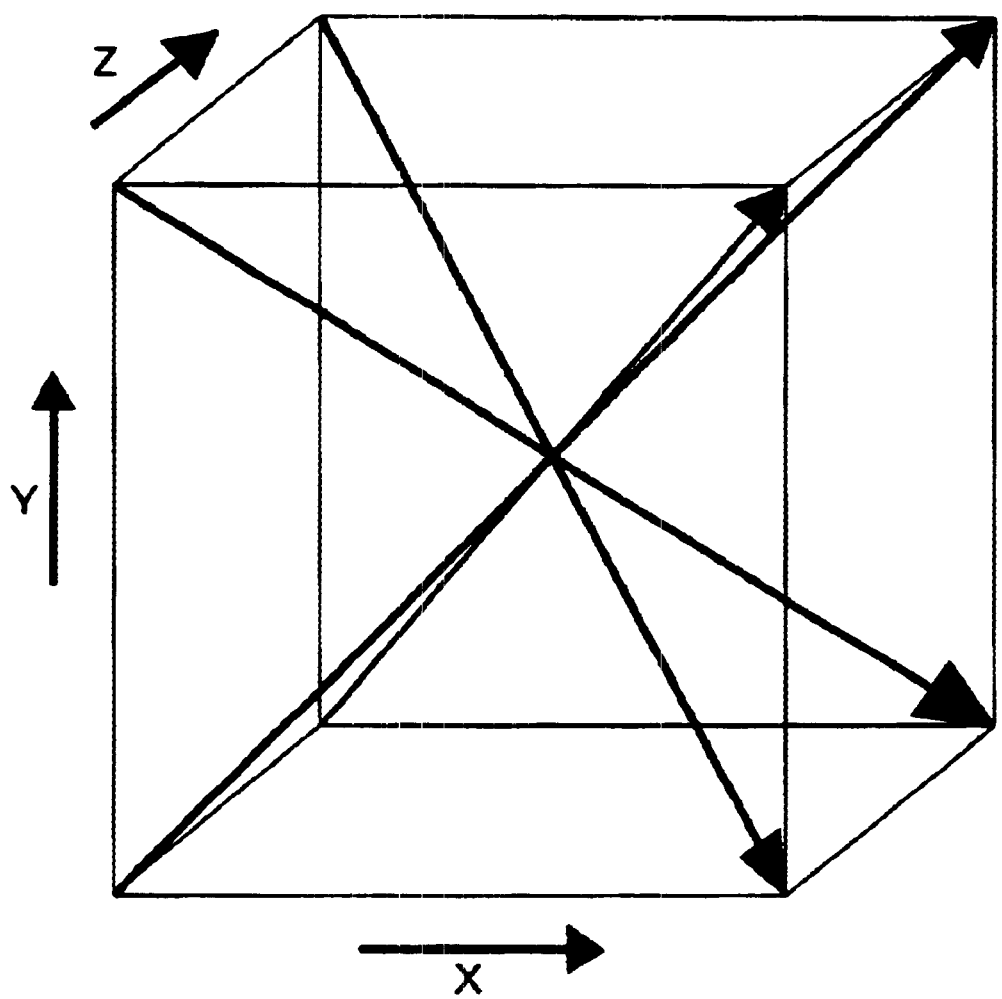
FIG. 5 is a schematic diagram illustrating the relative orientation of the spatial-encoding magnetic field gradients in a Hadamard multiplexed MR tracking procedure; and, FIG. 6 is a signal intensity profile of a tracking coil under worst case conditions to which embodiments of the present invention are applicable.

It is to be appreciated that no a priori assumption can be made about the orientation of the coil. During an interventional procedure, the orientation of the coil typically varies. Thus, it is desirable for the tracking system to be capable of tracking the coil(s) in any orientation. Furthermore, MR tracking is performed by acquiring data in response to multiple magnetic field gradient pulses. In the most widely used method, four excitations, each with a different spatial encoding gradient direction are employed and the resulting data is decoded using a system of linear equations (Hadamard de-multiplexing) to extract out the X, Y and Z coordinates of the coil. The relative geometry of these magnetic field gradients is shown in FIG. 5. Consequently, for every orientation of the tracking coil, there will be at least one excitation in which the MR signal profile is sub-optimal and has a profile similar to that shown in 210 of FIG. 4.

As described above, the maximum pixel technique would select the maximum pixel intensity to determine the location of the coil, or other tracking device. With sensitivity profiles such as 210 in FIG. 4, there is a problem with a sub-optimal MR signal profile since there are two peaks of high intensity which can lead to undesirable jitter artifacts about the indication of the location of the device. An embodiment of the present invention provides a method for tracking to overcome the problem of a sub-optimal profile. In principle, the acquired data could be fit to a parametric model of the sensitivity profile of a solenoid coil, but such an approach would be computationally intensive and probably marginal due to the number of parameters needed to define the fit. The method disclosed below is not computationally intensive and can be applied to all projections regardless of the orientation of the coil with respect to the applied magnetic field gradient.

Figure 6:
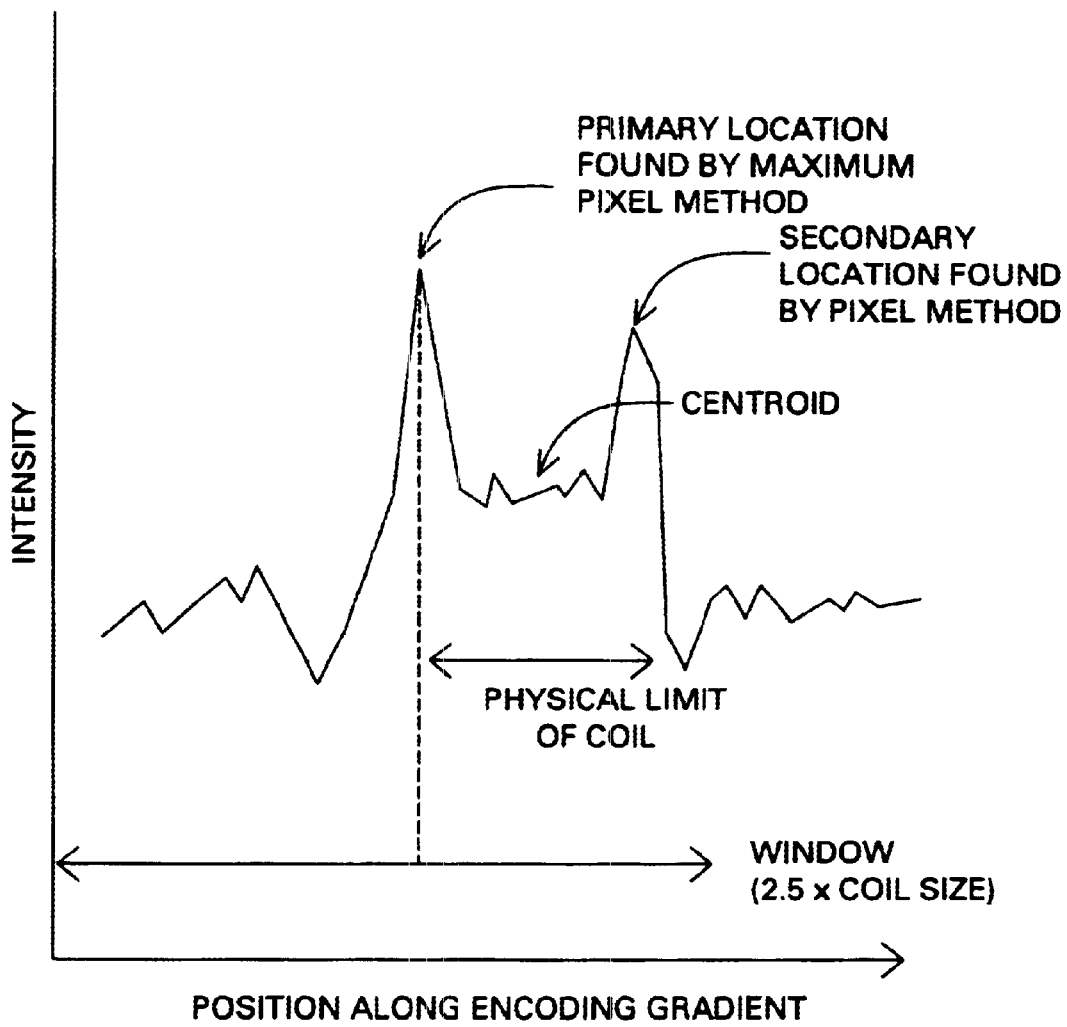

FIG. 6 illustrates a worst case profile of the tracking coil in which the coil is relatively large with respect to the Field-of-View (FOV) and the projection is made along the axis of the solenoid coil. With the conventional MR tracking algorithm, the maximum signal is identified and used as the location of the coil. Note that for a fully immersed coil, the location of maximum signal intensity occurs at one of the ends of the coil. If the coil is constructed to give a higher signal at one end and not the other (e.g. by over-winding one end), then the location of the coil will be robustly determined. If the coil has a symmetric sensitivity profile, however, then small fluctuations in the signal due to noise will cause the detected coil location to hop between the two maxima which contributes to the jitter artifact discussed above.

The present invention for tracking a coil within a field of view (FOV) of the MRI system utilizes an alternate method for determining the location of the coil. In this embodiment, a method for tracking a location of a device within a FOV of the MRI system comprises computing the location of the centroid of signal intensity in a region centered about a location of maximum signal intensity, $L_{max}$ of MR signals acquired for the device. As used herein, "centroid" refers to a central region of intensity and is computed as a function of the intensities found in a region including the length of the device. The region is a window W having a length greater than the length of the device to be sufficient to encompass all the signals from the device. Computing the centroid of signal intensity in the region encompassing the length of the coil provides a tracking system with reduced jitter artifact. Additionally, the computations do not depend on coil orientation and location parameters, which vary during the course of an interventional procedure.

In accordance with this embodiment, rather than simply finding the location of the maximum signal, the coil position is computed using the following steps:

1) find the location in the frequency-domain of the maximum signal intensity of acquired MR signals from the device. Let this location be called $L_{max}$.

2) determine the approximate number of pixels which cover the length of the coil. Let this number be called C.

3) select an expansion factor, F, which when multiplied by C will provide a window W. When this window, W, is centered at $L_{max}$ it will be large enough to encompass all the signals from the coil, regardless of which maximum is detected in step 1. A convenient value for P is 2.5.

4) compute the location of the centroid, $L_{cent}$ of signal intensity in the region W centered about the location $L_{max}$. The location of the centroid can be computed as:

$$L_{cont} = \frac{\sum_{i=L_{max}-W/2}^{L_{max}+W/2} i * \text{Intensity}(i)}{\sum_{i=L_{max}-W/2}^{L_{max}+W/2} \text{Intensity}(i)} \quad (2)$$

where intensity(i) is the pixel intensity of the ith data point in the projection.

Note that for the worst case profile shown in FIG. 6, the location of the centroid will be approximately the same, regardless of which maximum is found in the worst case profile. This location is approximately in the center of the coil. Furthermore, the algorithm will return the location of the maximum signal (i.e. also the center of the coil) for more predicable profiles such as the best case profile (220) shown in FIG. 4.

While several presently preferred embodiments of the novel tracking system have been described in detail herein, many modifications and variations will now become apparent to those skilled in the art. It is, therefore, to be understood that the appended claims are intended to cover all such modifications and variations as fall within the true spirit of the invention.

What is claimed is:

1. A method for tracking the location of a device within the field of view of a Magnetic Resonance Imaging (MRI) system comprising:

computing a centroid of signal intensity in a region centered about a location of maximum signal intensity, $L_{max}$ of acquired magnetic resonance (MR) signals from the device; and, locating the device based on the signal intensity.

2. The method of claim 1 wherein the region has a length greater than a respective length of the device.

3. The method of claim 1 wherein the device comprises a guide wire, a catheter, an endoscope, a laparoscope, a biopsy needle, an ablation device or non-invasive, external coils used in tracking.

4. The method of claim 1 wherein the computing step is performed according to:

$$L_{cent} = \frac{\sum_{i=L_{\max}-W/2}^{L_{\max}+W/2} i * \text{Intensity}(i)}{\sum_{i=L_{\max}-W/2}^{L_{\max}+W/2} \text{Intensity}(i)}$$

where $L_{max}$ is a maximum signal intensity, W is a region centered at $L_{max}$, and intensity(i) is a pixel intensity of the ith data point in a set of frequency-domain MR signals from the device.

5. The method of claim 1 further comprising displaying the location on a display device coupled to the MRI system.

6. A method for tracking the location of a device within the field of view (FOV) of a Magnetic Resonance Imaging (MRI) system comprising:
   finding a location of maximum signal intensity, $L_{max}$ of acquired magnetic resonance (MR) signals from to the device;
   determining an approximate number of pixels which cover the length of the device, C;
   selecting an expansion factor, F, which when multiplied by C will provide a region W, W being centered at $L_{max}$ and having a length sufficient to encompass all the signals from the device;
   computing a location of a centroid, $L_{cent}$ of signal intensity in the region W centered about the location $L_{max}$ in accordance with:

$$L_{cent} = \frac{\sum_{i=L_{\max}-W/2}^{L_{\max}+W/2} i * \text{Intensity}(i)}{\sum_{i=L_{\max}-W/2}^{L_{\max}+W/2} \text{Intensity}(i)}$$

where intensity(i) is a pixel intensity of the ith data point in the projection; and,
   locating the device based on the signal intensity.

7. The method of claim 6 wherein the device comprises a guide wire, a catheter, an endoscope, a laparoscope, a biopsy needle, an ablation device or non-invasive, external coils used in tracking.

8. The method of claim 6 further comprising displaying the location of the tracking device on a display device coupled to the MRI system.

9. A system for tracking the location of a device within the field of view (FOV) of a Magnetic Resonance Imaging (MRI) system comprising:
   a locator sub-system adapted to compute a centroid of signal intensity in a region centered about a location of maximum signal intensity, $L_{max}$ of acquired magnetic resonance (MR) signals from the device and locate the device based on the signal intensity; and,
   a display device coupled to the locator sub-system for displaying the location of the device.

10. The system of claim 9 wherein the device comprises a guide wire, a catheter, an endoscope, a laparoscope, a biopsy needle, an ablation device or non-invasive, external coils used in tracking.

11. The system of claim 9 wherein the locator sub-system is adapted to compute the centroid according to:

$$L_{cent} = \frac{\sum_{i=L_{\max}-W/2}^{L_{\max}+W/2} i * \text{Intensity}(i)}{\sum_{i=L_{\max}-W/2}^{L_{\max}+W/2} \text{Intensity}(i)}$$

where $L_{max}$ is the maximum signal intensity, W is a region centered at $L_{max}$, and intensity(i) is a pixel intensity of the ith data point in a set of frequency-domain MR signals from the device.

* * * * *